United States Patent [19]

Rossi et al.

[11] Patent Number: 4,613,694
[45] Date of Patent: Sep. 23, 1986

[54] PREPARATION OF UNSATURATED OR SATURATED α, ω-DIALDEHYDES AND α, ω-DIACIDS

[75] Inventors: Pier P. Rossi, Garlasco; Salvatore Marchetti, Cesano Maderno, both of Italy

[73] Assignee: Snia Viscosa Societa' Nazionale Industria Applicazioni Viscosa S.p.A., Milan, Italy

[21] Appl. No.: 192,478

[22] Filed: Sep. 30, 1980

[30] Foreign Application Priority Data

Oct. 5, 1979 [IT] Italy ................. 26292 A/79

[51] Int. Cl.$^4$ ............ C07C 45/40; C07C 45/59; C07C 51/34
[52] U.S. Cl. .................. 562/590; 562/595; 568/469; 568/483
[58] Field of Search .......... 562/590, 595; 568/483, 568/469

[56] References Cited

U.S. PATENT DOCUMENTS

| 2,819,279 | 1/1958 | Brown et al. | 260/413 |
| 2,865,937 | 12/1958 | Maggiolo | 562/590 |
| 3,091,620 | 5/1963 | Sturrock et al. | 568/469 |
| 3,979,450 | 9/1976 | Moskovich et al. | 562/590 |

FOREIGN PATENT DOCUMENTS

| 374277 | 7/1973 | U.S.S.R. | 562/590 |
| 556135 | 6/1977 | U.S.S.R. | 562/590 |

*Primary Examiner*—Vivian Garner
*Attorney, Agent, or Firm*—Stiefel, Gross, Kurland & Pavane

[57] ABSTRACT

Process for the concurrent preparation of olefinically unsaturated or saturated α,ω-dialdehydes and α,ω-diacids, characterized by the fact that the monoozonide of a a mono- or polyunsaturated cycloolefine in solution in a polar solvent, is treated with water and subsequently with an alkaline aqueous solution at room pressure and at a temperature from −5° C. to 70° C., maintaining during the addition of the alkali, a pH not higher than 12, the dialdehyde and the diacid being subsequently isolated by known, conventional methods.

8 Claims, No Drawings

PREPARATION OF UNSATURATED OR SATURATED α, ω-DIALDEHYDES AND α, ω-DIACIDS

BACKGROUND OF THE INVENTION

1. Field of the Invention

The present invention refers to a process for the concurrent preparation of unsaturated or saturated α,ω-dialdehydes and α,ω-diacids. The present invention further refers to said dialdehydes and said diacids prepared by the aforesaid process.

2. Prior Art

In Italian Application No. 30939 A/76 corresponding to U.S. Pat. No. 4,177,214 the preparation is described of unsaturated α,ω-dialdehydes starting from the monoozonides of the corresponding polyunsaturated cycloolefins, while in Italian Applications No. 28802 A/75 corresponding to Italian Pat. No. 1,049,005 and No. 29682 A/78 corresponding to U.S. application Ser. No. 090,987, abandoned, the preparation is described of the α,ω-dicarboxylic acids, by oxidation of the corresponding dialdehydes or the corresponding aldehydo-acids.

In the preparation of the unsaturated α,ω-dialdehydes according to Italian Application No. 30939 A/76, the dialdehyde is obtained by selective reduction of the corresponding unsaturated ozonides, by means of hydrogen under pressure and of a particular catalytic system constituted by the combination of two metals, while in Italian Applications No. 28802 A/75 and No. 29682 A/78 the dicarboxylic acids are obtained by catalytic oxidation of the dialdehydes or the aldehydo-acids using air and a catalyst based on cobalt and/or silver.

The unsaturated diamines are obtained from the unsaturated dialdehydes by reductive amination; the saturated and/or unsaturated diamines and the saturated and/or unsaturated diacids may be used to prepare unsaturated polyamides, e.g. according to the Italian Application No. 26291 A/79 corresponding to German DOS No. 3037488 Al by the same Applicant.

It is obvious that in order industrially to produce said two monomers two production lines are required, the first one for preparing the diamines and the second one for preparing the diacids, which involves a double investment and an increased production cost.

SUMMARY OF THE INVENTION

The Applicant has now surprisingly found a process by which it is possible concurrently to obtain the saturated or olefinically unsaturated dialdehyde and the saturated or olefinically unsaturated diacid, by means of operations which occur under very moderate temperature and pressure conditions and in a single phase, using a single starting product, viz. the monoozonide of a mono- or polyunsaturated cycloolefin.

In contrast to the conventional methods which may lead to the formation of small amounts of dialdehyde and diacid as by-products, the present invention provides a method for obtaining said products as main products with high yields with respect to the monoozonide employed. Said yields of acid-dialdehyde exceed 60% by moles with respect to the monoozonide and reach values close to 100%.

The process which constitutes one of the objects of the present invention is characterized by the fact that the monoozonide of a mono- or polyunsaturated cycloolefine in solution in a polar solvent, is treated with water and subsequently with an alkaline aqueous solution at room pressure and at temperatures from $-5°$ C. to 70° C., maintaining a pH not higher than 12 during the addition of the alkali. Said reaction of the formation of dialdehyde and diacid from a cycloolefinic ozonide in aqueous medium is surprising if it is considered that when the operation is carried out in a rigorously anhydrous medium, in the presence of an anhydride of a carboxylic acid, according to what is described in U.S. Pat. No. 3.856.833 and in Italian Pat. No. 998.227 of the same Applicant, the corresponding aldehydo-acid is formed with yields which exceed viz. 90%. In such case two of the three oxygens of the cycloolefinic ozonide, represented by its classical formula, remain at one end of the molecule and the other oxygen at the other end, while when the process according to the invention is carried out, there are obtained from two cycloolefinic ozonide molecules, one molecule with two oxygens at each end of the molecule in the case of the α,ω-dialdehyde, and a second molecule with four oxygens, two at each end of the molecule in the case of the α,ω-diacid.

In particular there are formed:

(a) according to the known processes:

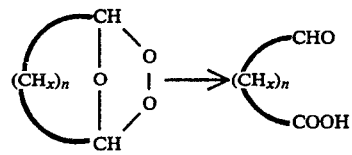

(b) according to the process of the invention:

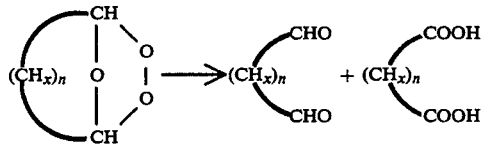

wherein
x=1 and/or 2
n=from 4 to 10.

If the starting product is the ozonide of a monounsaturated cycloolefine, the products obtained are the saturated diacid and the saturated dialdehyde, whereas if the starting products is the monoozonide of a polyunsaturated cycloolefine, the products obtained are the corresponding unsaturated diacid and the unsaturated dialdehyde.

DETAILED DESCRIPTION OF THE PREFERRED EMBODIMENTS

The products which can be used according to the invention, are the monoozonides of mono- or polyunsaturated cycloolefines having preferably from 6 to 12 carbon atoms, e.g. the monoozonides of cyclohexene, cyclooctene, cyclooctadiene, cyclodecene, cyclodecadiene, cyclododecene and cyclododecatriene, obtained, e.g., according to one of the patents of the Applicant: U.S. Pat. No. 3.856.833 and Italian No. 998.227, and preferably dissolved in at least one polar solvent, such as e.g., a saturated aliphatic carboxylic acid containing from 2 to 14 carbon atoms of the type of acetic, propionic and pelargonic acid. Before subjecting the ozonide solution to the reaction which forms an object of the present invention and which will be called hereinafter, for simplicity's sake, "dismutation", it is convenient to carry out an extraction of the ozonide solution in the polar solvent with a liquid hydrocarbon, e.g., cyclohexane, to remove all amounts of unreacted cycloolefine which may be present and may still be dissolved in the solutions of the ozonide in the polar solvent.

Generally the ozonide is dissolved in the polar solvent in concentration from 20 to 50%, if the solution is too much diluted, it is convenient to concentrate it under a vacuum before the treatment with water and then with the alkali solution.

The hydroxides of alkali and alkaline earth metal metals or the carbonates of the alkali metals may be used as alkalies.

The preferred conditions are: ozonide concentration in the solvent 25–50% by weight, temperature from 5° to 25° C., room pressure, pH from 8 to 12, use of sodium hydroxide as alkaline base. It is possible to operate not only with the polar solvent alone but also in the presence of a hydrocarbon solvent, e.g., cyclohexane, which promotes the separation as it tends to dissolve the dialdehyde as it is formed, while the dicarboxylic acid remains dissolved in the aqueous phase in the form of the salt of the alkali or earth-alkali metal which has been added. The control of the pH of the solution is conveniently effected with an electronic instrument for measuring the pH chosen among those normally used in chemical operations.

The solution of monoozonide (obtained, e.g., according to one of the examples of the U.S. Pat. No. 3.856.833 or Italian No. 998.227) is extracted with hydrocarbon solvent, e.g. cyclohexane, is concentrated under a vacuum to a concentration close to 50%, and is suspended in water, the water is separated by decantation. Thereafter the pH measuring electrode is immersed in the reaction vessel and is connected to a suitable indicator instrument, the temperature is brought from 10° C. to 18° C. by external cooling of the reaction vessel and the alkali hydroxide (or carbonate) aqueous solution is added at such a rate as to maintain the pH at the predetermined value, which is anyway lower than 12. Generally, after the initial phase, the pH value increases at each addition of the alkaline solution and thereafter decreases with time and finally becomes stabilized. The reaction is considered to be ended when the pH value does not decrease at a further addition. It is also possible to follow the progress of the ozonide conversion by the titration of the active or peroxidic oxygen, by analysis with a potassium iodide solution, according to the classic peroxide analysis method. At the end of the reaction the dialdehyde is decanted from the underlying liquid or even extracted, e.g., with ether, benzene or cyclohexane.

The carboxyxlic acid is suitably recovered from the aqueous solution in which it is in the form of salt, by acidifying it, e.g., with sulphuric acid.

A further object of the present invention is the saturated or unsaturated $\alpha,\omega$-dialdehyde and the saturated or unsaturated $\alpha,\omega$-diacid obtained by the process of the present invention.

The following examples are illustrative but not limitative.

The parts are parts by weight unless otherwise specified.

EXAMPLE 1

Preparation of the dodeca-4,8-diene-1,12-dioic acid and of the dodeca-4,8-diene-1,12-dialdehyde by "dismutation" of the monoozonide of cyclododecatriene 1100 parts of a solution of the monoozonide of cyclododecatriene in acetic acid, obtained in a manner analogous to what is described in example 1 of Italian Pat. No. 998.227, however in the absence of acetic anhydride, having an active oxygen titre of 3.75 meq/g (corresponding to a total of 4125 meq, viz.

$$\frac{4125 \cdot 210}{1000 \cdot 2} = 433.12$$

parts of ozonide) are extracted with cyclohexane (5 extractions with 300 parts of cyclohexane each time).

After the extraction 1020 parts of acetic solution of ozonide remain, having the titre 3.975 meq/g (corresponding to a total of 4054.5 meq, viz. to 425.7 parts of ozonide).

500 parts of said ozonide acetic solution, containing 208.6 parts of ozonide, is poured under stirring into a vessel provided with a bottom cock and a cooling jacket, containing 1050 parts of water. An oily top layer and a bottom aqueous layer are obtained. The bottom layer is drawn off. 200 parts of water are added again 4 times, and the decanted water is drawn off each time (total $H_2O$ 1850 parts).

2.95 parts of ozonide are found by iodometric analysis in said water, so that the remaining ozonide is 205.65 parts.

250 parts of water are added to the remaining oil and a thermometer and an electrode for measuring the pH are introduced into the vessel, while cooling the jacket of the vessel by circulation of water at 16° C.

A 9.944% NaOH aqueous solution is charged into a dripping funnel placed on the lid of the vessel and the dripping is begun under stirring. The following data have been found:

| Time (minutes) | Temperature °C. | pH | NaOH added (parts by volume) |
| --- | --- | --- | --- |
| 0 | 16 | 2 | 0 |
| 5 | 18 | 10.5 | 16 |
| 20 | 19 | 10.5 | 100 |
| 35 | 20 | 9.5 | 200 |
| 40 | 20 | 8.0 | 200 |
| 55 | 19 | 10.5 | 300 |
| 80 | 19 | 10.8 | 400 |
| 90 | 21 | 10.5 | 500 |
| 102 | 21 | 10.8 | 600 |
| 117 | 20 | 10.5 | 700 |
| 135 | 20 | 10.7 | 750 |
| 145 | 20 | 11.0 | 755 |

The addition of the NaOH solution is then discontinued and the product is allowed to rest overnight.

Two phases are present in the vessel, an upper oily phase and a lower aqueous phase. Peroxidic oxygen is present in traces in the oily layer, while it is absent in the aqueous layer.

The NaOH solution added has been found to be 880 parts at 9.944% concentration, corresponding to 87.5 parts of an anhydrous NaOH, corresponding to 2.19 parts by moles. The ozonide charged in 205.65 parts, viz. 0.98 parts by moles. The reaction product is extracted with ether, the ether solution is dried over sodium sulphate, it is evapotated to dryness and a residue is obtained of 113.8 parts of raw dodeca-4,8-diene-1,12-dialdehyde having the following analytic titres

|  | Calculated for the dodeca-4,8-diene-1,12-dialdehyde | Found for the dodeca-4,8-diene-1,12-dialdehyde |
| --- | --- | --- |
| Aldehyde groups (meq/g) (with $H_2NOH-HCl$) | 10.3 | 9.5 |
| Double bonds (in moles $H_2/g$) (by hydrogenation) | 10.3 | 9.8 |

The product obtained is a straw colored oil which has a boiling point of 101°–103° C. at 0.07 mmHg, which is purified by distillation.

The aqueous phase which remains after extraction with ether is acidified with diluted $H_2SO_4$ to pH 1 and is extracted once more with ether. The ether is washed with water, is dried over sodium sulphate and evaporated to dryness.

A residue (101.6 parts) is obtained which melts at 58°–60° C. and is constituted by raw dodeca-4,8-diene-1,12-dioic acid, as shown by the following analytical data.

|  | Calculated for dodeca-4,8-diene-1,12-dioic acid | Found for dodeca-4,8-diene-1,12-dioic acid |
| --- | --- | --- |
| Acidity meq/g | 8.85 | 8.6 |
| Double bonds (moles $H_2/g$) | 8.85 | 8.5 |

We claim:

1. A process for the concurrent preparation of olefinically unsaturated or saturated $\alpha,\omega$-dialdehydes and $\alpha,\omega$-diacids, comprising treating a solution of a monoozonide of a mono- or polyunsaturated cycloolefin and a polar solvent by suspending said monoozonide solution in water and separating the water by decanting; subsequently adding an aqueous alkali solution wherein said alkali is selected from the group consisting of alkali metal hydroxides, alkaline earth metal hydroxides and alkali metal carbonates to the solution of monoozonide, at room pressure and a temperature from $-5°$ C. to 70° C.; maintaining, during said addition of alkali, a pH from about 8 to 12; and isolating the resulting dialdehyde and the diacid.

2. Process according to claim 1, wherein the monoozonide of a cycloolefine contains from 6 to 12 carbon atoms.

3. Process according to claim 2, wherein the monoozonide of cyclohexene, cyclooctene, cyclooctadiene, cyclodecene, cyclodecadiene, cyclododecene or cyclododecatriene is used.

4. Process according to any one of claims 1, 2 or 3, further comprising subjecting the monoozonide, polar solvent solution to extraction with a liquid hydrocarbon before the water treatment.

5. Process according to claim 4, wherein said polar solvent is an aliphatic carboxylic acid.

6. Process according to claim 4, wherein cyclohexane is said liquid hydrocarbon.

7. Process according to any one of claims 1, 2 or 3 wherein the concentration of the monoozonide in the polar solvent is between 20 and 50% by weight.

8. The process according to any one of claims 1, 2 or 3 further comprising adding a hydrocarbon solvent to said polar solvent.

* * * * *